United States Patent [19]

Hegland et al.

[11] Patent Number: 4,980,902
[45] Date of Patent: * Dec. 25, 1990

[54] APERTURE MEASURING SYSTEM FOR CORD REINFORCED TIRE FABRIC

[75] Inventors: Philip M. Hegland; Lee M. Chase, both of Cupertino, Calif.

[73] Assignee: Measurex Corporation, Cupertino, Calif.

[*] Notice: The portion of the term of this patent subsequent to Nov. 10, 2004 has been disclaimed.

[21] Appl. No.: 814,486

[22] Filed: Dec. 30, 1985

[51] Int. Cl.⁵ ............................................. G01N 23/02
[52] U.S. Cl. .................................. 378/61; 250/359.1; 250/358.1
[58] Field of Search ................ 378/61, 58; 250/358.1, 250/359.1, 360.1

[56] References Cited

U.S. PATENT DOCUMENTS

| | | | |
|---|---|---|---|
| 3,497,693 | 2/1970 | Duftschmid et al. | 378/56 |
| 3,727,054 | 4/1973 | Herrick | 378/61 |
| 3,757,122 | 9/1973 | Bossen et al. | 378/55 |
| 3,854,046 | 12/1974 | Wood | 378/58 |
| 3,889,121 | 6/1975 | Bossen | 250/359 |
| 3,914,607 | 10/1975 | Cho et al. | 250/308 |
| 4,165,461 | 8/1979 | Ishijima | 378/61 |
| 4,389,136 | 6/1983 | Fehrenbach | 250/308 |
| 4,706,267 | 11/1987 | Chase et al. | |

FOREIGN PATENT DOCUMENTS

| | | | |
|---|---|---|---|
| 1225396 | 9/1966 | Fed. Rep. of Germany . | |
| 2555135 | 6/1976 | Fed. Rep. of Germany . | |
| 0060345 | 4/1984 | Japan | 378/58 |
| 1312771 | 9/1973 | United Kingdom . | |

OTHER PUBLICATIONS

Commonly assigned related co-pending U.S. Patent Application No. 06/804,384 to Chase, et al. with claims as most recently amended.

Primary Examiner—Craig E. Church
Assistant Examiner—John C. Freeman
Attorney, Agent, or Firm—Spensley Horn Jubas & Lubitz

[57] ABSTRACT

A system for measuring the open space between, and the ratio of open space to cord diameter, of cord reinforced tire fabric. A collimated x-ray source and detector scan across the tire fabric as it is calendered providing a signal corresponding to each edge of a cord. A counter counting at a constant rate provides a time interval measurement of each open space, and also of the corresponding open space plus cord, as the x-ray source and detector scans the fabric. The quotient of the two time intervals determined is proportional to the fractional open space at a particular location in the fabric. An alarm is provided to indicate when the open space is outside predetermined limits.

9 Claims, 4 Drawing Sheets 4,980,902

APERTURE MEASURING SYSTEM FOR CORD REINFORCED TIRE FABRIC

BACKGROUND OF THE INVENTION

Cord reinforced tire fabric is commonly made in a continuous calendering process which results in a sandwich including multiple strands of cord with a layer of rubber on each side. It is essential to the strength of the fabric and the resulting tire that the space between the tire cords not exceed some specified value. The maximum value could be exceeded, for example, if cords are out of position, missing, if the cord diameter varies, or a combination of the preceding. Similarly, it is important that the space between cords not be too small. This is because the rubber latex which makes up the body of the fabric is applied from both sides of the cord core, and it is essential that the latex be able to easily flow between the cords and coalesce into a single mass.

A system which merely counts the number of cords per inch is not satisfactory since such a system gives only the average spacing and cannot detect a single space fault.

The open space (aperture) between tire cords is significant not only because of its relationship to the strength of the product, but it is also useful in the continuous determination of the basis weight of product as it is being manufactured. One method of determining basis weight involves measuring the amount of beta ray radiation passing through the fabric. Since the cord spacing affects the beta ray transparency of the fabric, a correction to the basis weight calculation from beta ray measurements is required. The present invention provides a signal which can be used for such a correction.

SUMMARY OF THE INVENTION

The present invention is particularly useful in connection with steel cord reinforced tire fabric, and is thus explained in connection with this type of fabric. It should be understood, however, that the principles described herein can be used in connection with other types of reinforcing cord, so long as the radiation absorption coefficient of the cord material is different from the rubber used.

It is an object of the present invention to measure the aperture between the cords of cord reinforced tire fabric with a system which is independent of cord diameter. The factor which is significant is not simply the absolute value of the open space between cords, but rather the fraction of the total space which is open. The invented system involves scanning the tire fabric at a constant speed using a highly collimated X-ray beam directed through the fabric. Substantially all of the X-ray energy is absorbed by the steel cord, but a significant part of the energy is transmitted through the rubber portion of the fabric. An X-ray detector on the other side of the fabric therefore receives a varying amount of radiation as the fabric is scanned. A timing control signal corresponding to each transition between cord and open space gates a counter which counts cycles of a fixed frequency oscillator in such a way as to result in data representing the cord to cord spacing and also the open space between cords. This data is manipulated to achieve the desired information and to trigger an alarm if predetermined limits are exceeded.

DETAILED DESCRIPTION OF THE INVENTION

Figure 1:
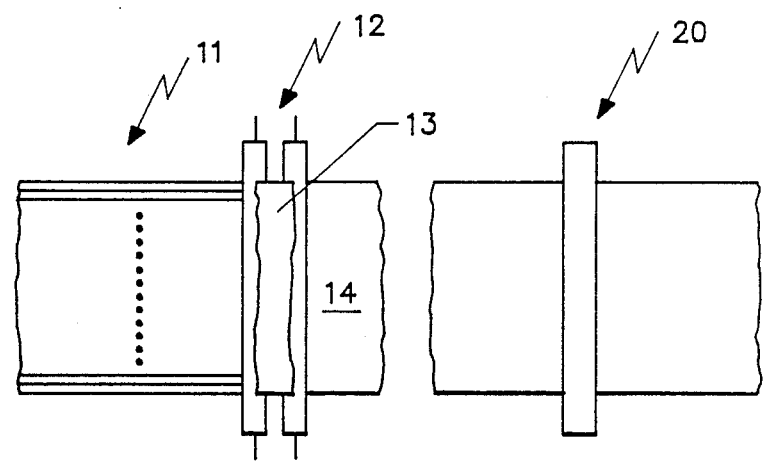
FIG. 1 is a diagrammatic plan view of a steel cord reinforced tire fabric calendar which may be used in connection with the present invention.

FIG. 1 shows a highly diagrammatic plan view of a steel cord tire fabric calendar such as may be used in connection with the present invention. Steel cord tire fabric is typically made in widths of about four feet and is usually provided with about 5 to 20 reinforcement cords per inch of width. As shown in FIG. 1, the steel cords 11 enter from the left of the machine and pass under calendar rolls 12 which deposit a sheet of latex on top of the travelling cords. The latex pool 13 on top of the rolls 12 is kept replenished by means not shown. A second set of calendar rolls (also not shown) are located under the plane of the travelling cords, and apply a similar sheet of latex to the under side of the cords. As the sheets of latex are applied, they flow between the cords and coalesce into a single entity. The fabric leaving the rolls is thus a sheet of latex with a core of spaced steel reinforcing cord.

Figure 2:
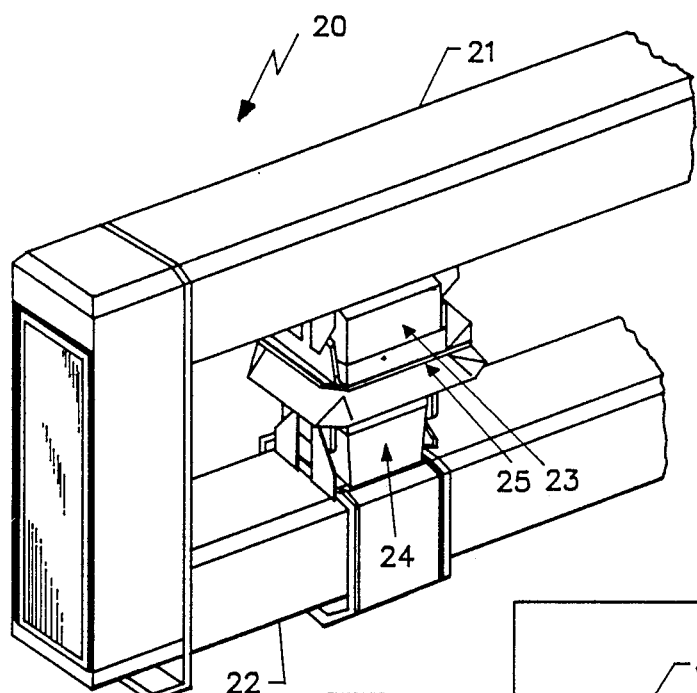
FIG. 2 is a perspective view of a portion of the monitor section of the present invention.

After leaving the calendar rolls, and possibly after some further processing, the fabric is passed through a monitor section 20 to determine certain of its characteristics. One such characteristic which may be monitored is the open space (i.e., the aperture) between cords as a fraction of the cord to cord spacing. The monitor section, which holds the sensing portion of the invented apparatus, includes upper and lower traverse beams 21 and 22 as can be seen in FIG. 2. The upper and lower traverse beams are located, as their names imply, over and under the fabric web.

X-ray source head 23 and sensor head 24 are mounted to the upper and lower traverse beams respectively such that they can move back and forth on the beams, with the fabric wet passing in the space 25 between them. Means not shown keeps the X-ray source and sensor in alignment, and causes both to scan back and forth across the width of the fabric at constant speed.

Figure 3:
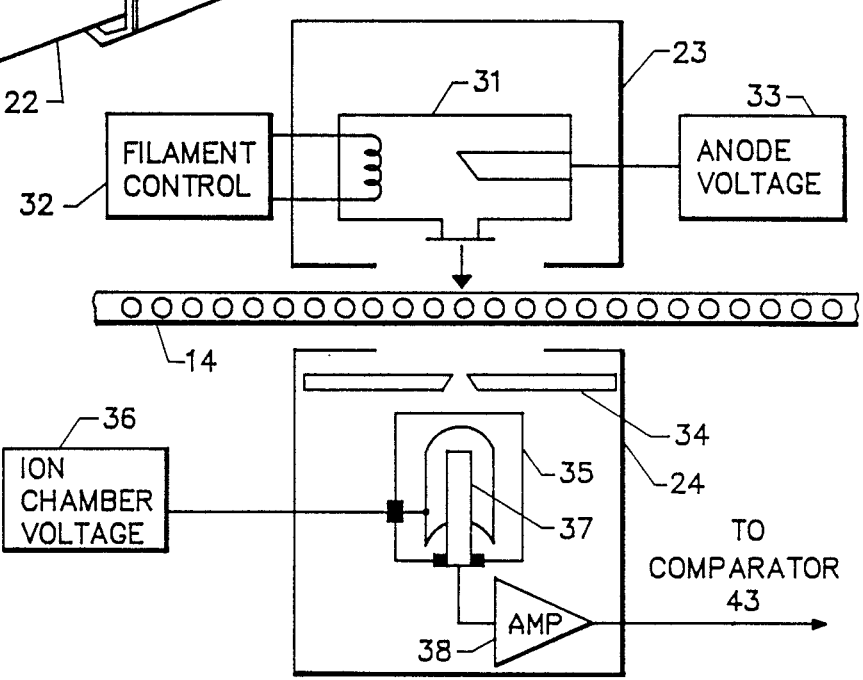
FIG. 3 is a diagrammatic cross sectional view of the X-ray source and sensor of the present invention.

FIG. 3 shows the arrangement of X-ray source head 23 and sensor head 24. X-ray tube 31, energized by filament control 32 and anode voltage source 33, emits a relatively narrow X-ray beam downward through fabric 14 and aperture slit 34 into ionization chamber 35. The aperture slit width is typically 0.010 inch which provides a narrow beam and good definition of the edges of the cords. Ionization within chamber 35 permits a current to flow from the ionization chamber voltage source 36 to central electrode 37. The operation of ionization chamber detectors for the measurement of X-rays is well known, so that it is not believed necessary to explain the operation of this portion of the invention in more detail. It is sufficient to note that when one of the steel cords of tire fabric 14 blocks the X-ray beam, the output of amplifier 38 is low, but when only rubber is between the X-ray tube and the ionization chamber the amplifier output is high.

Figure 5:
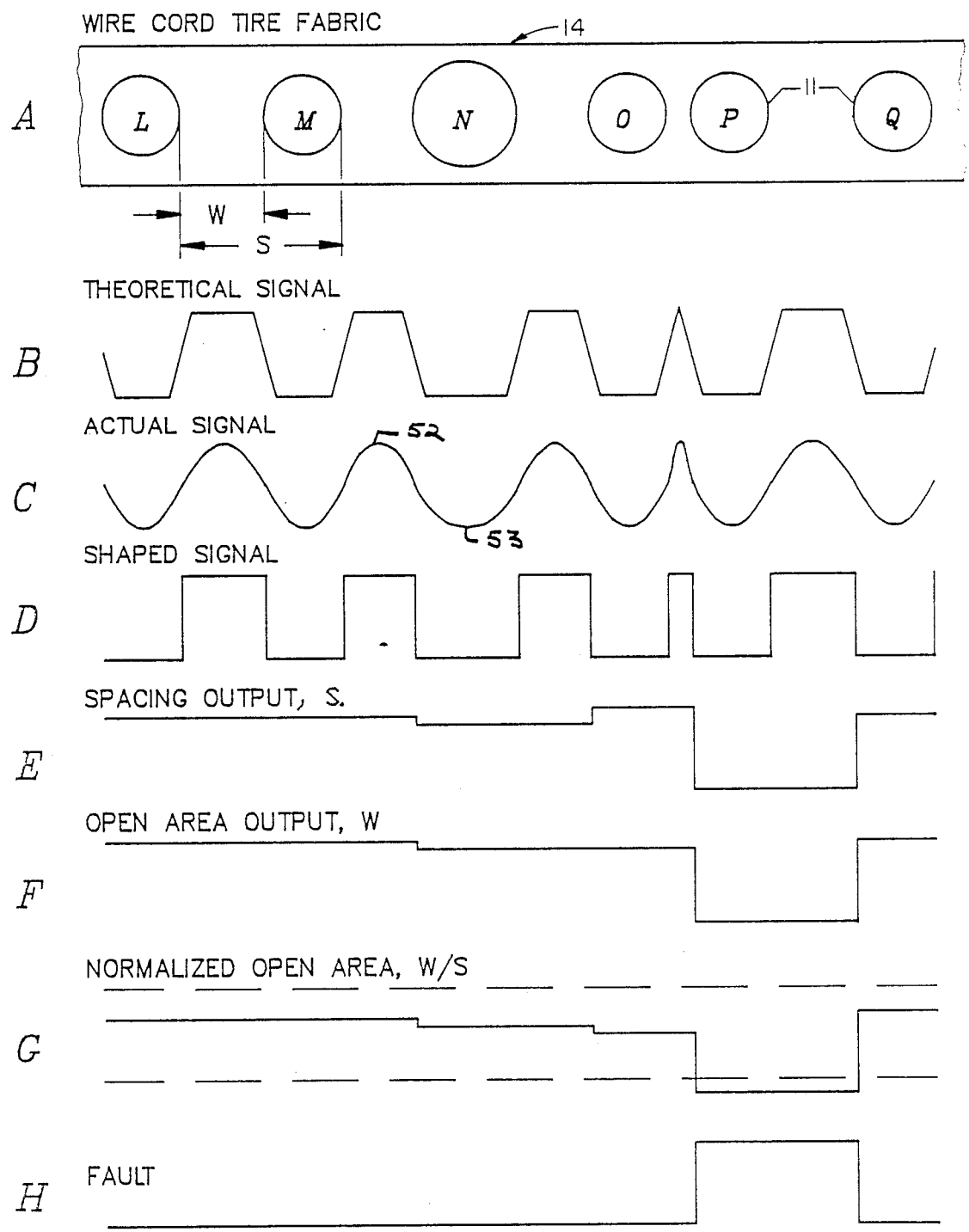
FIG. 5 shows various waveforms generated in the electronic portion.

For purposes of illustration, a small section of tire fabric is shown in FIG. 5 along with waveforms that would be generated by the electronic circuitry of the present invention during a traverse by the sensing elements (23, 24) from left to right. FIG. 5a shows the fabric section including cords L-Q. As can be seen, the center to center spacing of all but O/P are the same. The O/P spacing is less than the others and is shown, for purposes of example to be so small as to trigger a fault alarm.

As the X-ray source/sensor 23, 24 traverses the slice of cord illustrated in FIG. 5A, an undulating waveform appears at the output of amplifier 38. Ideally, the waveform is trapezoidal as shown in FIG. 5B, but in actual practice the corners are rounded as shown in FIG. 5C. The slope of the leading and trailing edges of the ideal waveform 5B are due to the finite diameter of the collimated X-ray beam, and the rounded corners of actual waveform 5C arise because of non-uniformities in the beam and the partial X-ray transparency of the cords.

Figure 4:
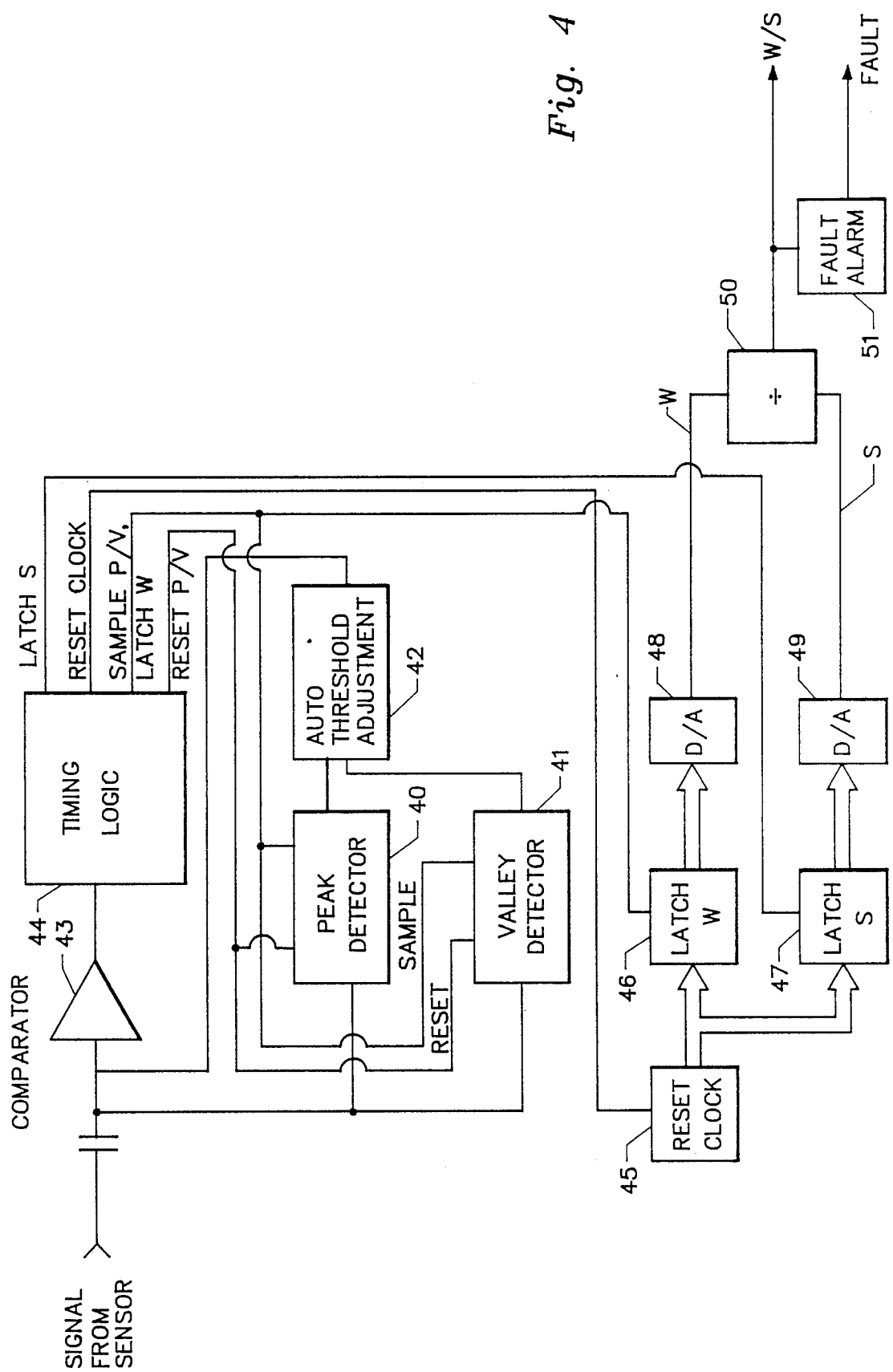
FIG. 4 is a block diagram of the electronic portion of the present invention.

The output of amplifier 38 is fed to peak detector 40 and valley detector 41 (FIG. 4) which hold the maximum and minimum voltages experienced, respectively, until reset. The maximum and minimum voltages held by the peak and valley detectors are fed to the automatic reference circuit 42 whenever the detectors (40, 41) receive a "sample" pulse from the timing logic module 44. In response to an input from the peak and valley detectors, the automatic reference circuit 42 generates a voltage approximately equal to one-half the peak plus valley voltage and couples this voltage to comparator 43 to act as a reference voltage for the comparator. Ideally, the reference voltage is equal to one half the peak plus valley voltage, but since the actual waveform of FIG. 5C may not be perfectly symmetrical, the required reference voltage may not be exactly the ideal voltage. The reference voltage is held until another sample pulse causes the voltage to change. The output of comparator 43 is the shaped signal of waveform 5D. It goes negative when the X-ray source/sensor passes the leading edge of a cord and positive at a trailing edge. The reference voltage may have to be adjusted slightly so that the transitions in the waveform of FIG. 5D occur when the X-ray beam is centered over a cord edge.

Figure 6:
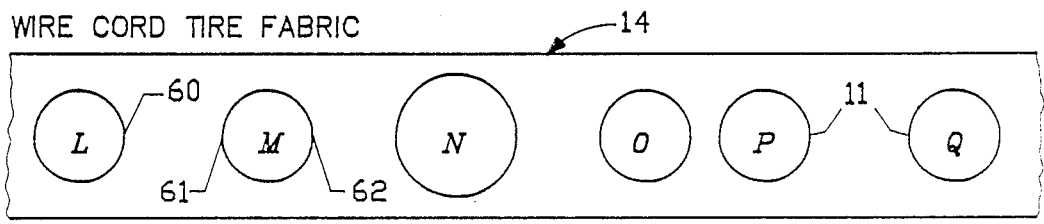
FIG. 6 is a timing diagram showing the relationship between the latching and reset functions.
Figure 6:
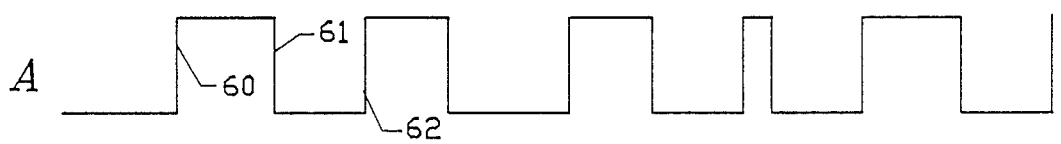
Figure 6:
Figure 6:
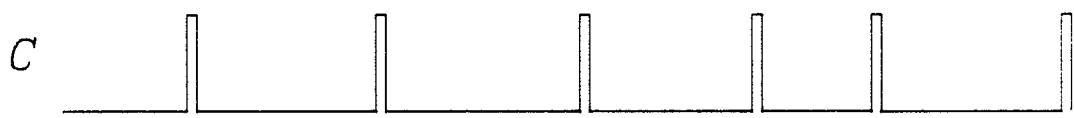
Figure 6:
Figure 6:

Timing logic module 44 is driven by comparator 43 and provides timing signals as shown in FIG. 6. As can be seen from the timing diagram of FIG. 6, the counter 45 is reset each time the X-ray beam leaves a cord and starts to traverse a space (shown, e.g., at 60 of FIG. 6). The counter 45 counts cycles of an internal fixed frequency oscillator. The frequency of the oscillator can, if desired, be correlated with the scan speed of the X-ray source/sensor so that the count in counter 45 will be numerically equal to the distance travelled by the source/sensor in whatever units of distance is convenient. When the space starting at 60 has been traversed and the X-ray beam is starting to traverse a cord (61), the count in counter 45, which is then representative of the width of the space (W in FIG. 5a,), is latched into latch 46. At the same time, a sample pulse is sent to the peak and valley detectors 40, 41. Immediately following the sample pulse, the peak and valley detectors are reset so as to be in condition to detect the maximum and minimum voltage generated during the next cycle, i.e., voltages 52 and 53 of FIG. 5.

The next cord edge detected (62) causes the count in counter 45, which at this time is proportional to the cord spacing (S in FIG. 5a), to be latched into latch 47. This is immediately followed by resetting of the counter for another cycle.

It may be noted that the reset pulses (FIGS. 6C and 6E) are shown on the timing diagram as apparently occurring at the same time as the latching pulses (FIGS. 6B and 6D). In actuality, the reset pulses occur slightly later in time so as not to interfere with the latching and sampling functions.

The counts in latches 46 and 47 are fed to D/A converters 48 and 49, the outputs of which are electrical signals proportional to the open space between cords (W) and the cord spacing (S) respectively. See waveforms 5E and 5F. Divider 50 provides the normalized open space signal (W/S) as shown in FIG. 5G. The dotted lines shown in FIG. 5G represent the specification limits of W/S, and alarm 51 will generate a spacing fault signal (FIG. 5H) when these limits are exceeded. As can be seen, in the example shown in FIG. 5, the limits are exceeded for the space between cords 0 and P. Had there been a large open space between any two cords of the example, alarm 51 would have also generated a fault signal corresponding to this fault.

What has been described is a presently preferred embodiment of a wire aperture measuring system for use in connection with the manufacture of wire cord reinforced tire fabric. It should be understood that while a presently preferred embodiment has been disclosed, various modifications within the spirit of the invention will no doubt occur to those skilled in the art and such modifications are intended to be covered by the following claims.

We claim:

1. A system for determining the open space between the cords of cord reinforced tire fabric, comprising:
   (a) a radiation source for providing a collimated beam of radiation through said tire fabric, said radiation being such that a greater amount of radiation will penetrate through the rubber of said fabric than through the cord of said fabric;
   (b) a detector for detecting said radiation aligned with said collimated beam of radiation and generating an electrical signal in response thereto;
   (c) means for causing said radiation source and said detector to scan across a section of said tire fabric at a predetermined speed;
   (d) means responsive to said electrical signal generated by said detector for providing a timing signal when said detector bears a predetermined relationship to each edge of the cords in said fabric said timing means includes:
   (i) means for detecting successive maximum and minimum values of said electrical signal;
   (ii) means for providing a reference voltage dependent on said maximum and minimum voltages, wherein said reference voltage has a magnitude equal to approximately one half of the sum of said maximum and minimum values of said electrical signal;
   (iii) comparator means for generating one timing signal each time said electrical signal equals said reference voltage; and
   (e) means for measuring elapsed times between occurrences of the timing signals, including means for determining the time required for said radiation source and detector to scan the distance between adjacent edges of two cords in said fabric.

2. A system for determining the position of cords in cord reinforced material, comprising:
(a) a radiation source directing a beam of radiation through the cord reinforced material;
(b) a detector for detecting said beam of radiation after the beam passes through the cord reinforced material, the width of the detected beam being less than the distance between adjacent cords of the reinforced material, and wherein said detector generates an electrical signal indicative of the intensity of the detected beam;
(c) means for causing said radiation source and detector to move in unison at a predetermined speed relative to a section of the cord reinforced material;
(d) means responsive to the electrical signal for providing a timing signal when said detector bears a predetermined relationship to each edge of the cords in said material, wherein said means for providing a timing signal includes:
(1) means for detecting successive maximum and minimum values of said electrical signal,
(2) means for providing a reference voltage dependent on said maximum and minimum values, and
(3) comparator means for generating one of said timing signals each time said electrical signal equals said reference voltage; and
(e) means for measuring elapsed times between occurrences of said timing signals.

3. The system of claim 2, wherein said reference voltage has a magnitude equal to approximately one half of the sum of said maximum and minimum values of said electrical signal.

4. A system for determining the position of cords in cord reinforced material, comprising:
(a) a radiation source directing a beam of radiation through the cord reinforced material;
(b) a detector for detecting said beam of radiation after the beam passes through the cord reinforced material, the width of the detected beam being less than the distance between adjacent cords of the reinforced material, and wherein said detector generates an electrical signal indicative of the intensity of the detected beam;
(c) means for causing said radiation source and detector to move in unison at a predetermined speed relative to a section of the cord reinforced material;
(d) means responsive to the electrical signal for providing a timing signal when said detector bears a predetermined relationship to each edge of the cords in said material, wherein said means for providing a timing signal includes:
(1) means for detecting successive maximum and minimum values of said electrical signal,
(2) means for providing a reference voltage dependent on said maximum and minimum values, and
(3) comparator means for generating one of said timing signals each time said electrical signal bears a predetermined relationship to said reference voltage; and
(e) means for measuring elapsed times between occurrences of said timing signals.

5. A radiation system for characterizing a cord reinforced material, comprising:
(a) a radiation source directing a beam of radiation through the cord reinforced material;
(b) a detector for detecting at least a portion of said beam of radiation after the beam passes through the cord reinforced material, the width of the detected beam being less than the distance between adjacent cords of the cord reinforced material, wherein said detector generates an electrical signal indicative of the intensity of the detected beam;
(c) means for causing said radiation source and detector to move in unison at a predetermined speed relative to a section of the cord reinforced material;
(d) means responsive to the electrical signal for providing a timing signal when said detector bears a predetermined relationship to each edge of the cords in said material, wherein the means for providing a timing signal includes:
(1) means for detecting successive maximum and minimum values of said electrical signal,
(2) means for providing a reference voltage dependent on said maximum and minimum values, and
(3) comparator means for generating one of said timing signals each time said electrical signal bears a predetermined relationship to said reference voltage; and
(e) means for measuring elapsed times between occurrences of said timing signals.

6. The radiation system of claim 5, wherein said means for measuring elapsed times includes means for determining a first scan time required for said radiation source and detector to scan the distance between adjacent edges of two cords in said cord reinforced material.

7. The system of claim 6, wherein said means for measuring elapsed times further includes means for determining a second scan time between one of said adjacent edges of two cords and the corresponding edge of the other of said two cords, said system further including means for determining the ratio of the value of said first scan time to the value of said second scan time.

8. A system for determining the open space between the cords of cord reinforced tire fabric which comprises:
(a) a radiation source for providing a collimated beam of radiation through said tire fabric, said radiation being such that a greater amount of radiation will penetrate through the rubber of said fabric than through the cord of said fabric;
(b) a detector for detecting said radiation beam, said detector being aligned with said collimated beam of radiation and generating an electrical signal in response thereto;
(c) means for causing said radiation source and said detector to scan across a section of said tire fabric at a predetermined speed;
(d) means responsive to said electrical signal generated by said detector for providing a timing signal when said detector bears a predetermined relationship to each edge of the cords in said fabric, where said means for providing a timing signal includes:
(1) means for detecting successive maximum and minimum values of said electrical signal;
(2) means for providing a reference voltage dependent on said maximum and minimum values; and
(3) comparator means for generating one of said timing signals each time said electrical signal equals said reference voltage; and
(e) means for measuring elapsed times between occurrences of said timing signals.

9. A radiation system for characterizing a cord reinforced material, comprising:
   (a) a radiation source for providing a beam of radiation;
   (b) a detector disposed to detect said radiation beam and with means generate an electrical signal in response thereto;
   (c) means for causing said radiation source and said detector to scan linearly back and forth at a predetermined speed;
   (d) means responsive to said electrical signal generated by said detector for providing timing signals wherein said means for providing timing signals includes:
      (1) means for detecting successive maximum and minimum values of said electrical signal;
      (2) means for providing a reference voltage dependent on said maximum and minimum values; and
      (3) comparator means for generating one of said timing signals each time said electrical signal bears a predetermined relationship to said reference voltage; and
   (e) means for measuring elapsed times between occurrences of said timing signals.

* * * * *